United States Patent
Dohi

(10) Patent No.: US 10,401,292 B2
(45) Date of Patent: Sep. 3, 2019

(54) OBSERVATION DEVICE

(71) Applicant: OLYMPUS CORPORATION, Tokyo (JP)

(72) Inventor: Masahito Dohi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/904,499

(22) Filed: Feb. 26, 2018

(65) Prior Publication Data
US 2018/0252648 A1 Sep. 6, 2018

(30) Foreign Application Priority Data

Mar. 1, 2017 (JP) ................. 2017-037920

(51) Int. Cl.
*G01N 21/64* (2006.01)
*G02B 21/00* (2006.01)
(Continued)

(52) U.S. Cl.
CPC ............ *G01N 21/6458* (2013.01); *G02B 5/12* (2013.01); *G02B 21/008* (2013.01); *G02B 21/0068* (2013.01); *G02B 21/0076* (2013.01); *G02B 21/0088* (2013.01); *G02B 21/10* (2013.01); *G01N 2021/6463* (2013.01); *G01N 2021/6478* (2013.01); *G01N 2201/0683* (2013.01); *G01N 2201/06113* (2013.01); *G02B 21/0032* (2013.01); *G02B 21/0048* (2013.01); *G02B 21/0084* (2013.01)

(58) Field of Classification Search
CPC ............ G02B 21/0032; G02B 21/0068; G02B 21/0076; G02B 21/008; G02B 21/10; G01N 2021/6478; G01N 21/6458; G01N 2201/06113; G01N 2201/0683

See application file for complete search history.

(56) References Cited

U.S. PATENT DOCUMENTS 6,238,911 B1    5/2001  Kasahara
8,591,836 B2 *  11/2013 Boege ................. B01L 3/50825
                                              422/552
2012/0301872 A1 11/2012 Tormod

FOREIGN PATENT DOCUMENTS

JP    H04-027909 A    1/1992
JP    H09-292572 A    11/1997
(Continued)

*Primary Examiner* — David P Porta
*Assistant Examiner* — Fani Boosalis
(74) *Attorney, Agent, or Firm* — Scully, Scott, Murphy & Presser, P.C.

(57) ABSTRACT

In the present invention, cells cultured inside the wells of a microplate are observed easily and clearly regardless of the height or curvature state of the liquid surface of the culturing liquid. Provided is an observation device that includes an illumination optical system that irradiates a transparent sample with illumination light from a light source, an objective lens that collects observation light from the sample, a detection optical system that detects the observation light collected by the objective lens, and a retroreflective member that is arranged opposite the objective lens with the sample interposed therebetween and in which a plurality of very small reflective elements are arrayed. The objective lens and the illumination optical system are arranged below the sample in the direction of gravity.

21 Claims, 12 Drawing Sheets

(51) Int. Cl.
　　　*G02B 21/10*　　　(2006.01)
　　　*G02B 5/12*　　　(2006.01)

(56) References Cited

FOREIGN PATENT DOCUMENTS

| | | |
|---|---|---|
| JP | 2000-004871 A | 1/2000 |
| JP | 2000-227556 A | 8/2000 |
| JP | 2013-511713 A | 4/2013 |
| WO | WO 2011/062548 A1 | 5/2011 |

* cited by examiner

10,401,292 B2

OBSERVATION DEVICE

CROSS-REFERENCE TO RELATED APPLICATIONS

This application is based on Japanese Patent Application No. 2017-037920, the contents of which are incorporated herein by reference.

TECHNICAL FIELD

The present invention relates to an observation device.

Heretofore, an observation method is known in which a cover composed of a microlens array that cancels out the refractive power of a liquid surface is arranged in order to prevent a problem of a lens effect being generated due to the liquid surface of a culturing liquid inside a well being curved due to surface tension in the case where cells that are accommodated along with a culturing liquid inside a plurality of small wells of a microplate are observed in their living state (for example, refer to PTL 1).

CITATION LIST

Patent Literature

{PTL 1} Japanese Unexamined Patent Application Publication No. 2000-4871

SUMMARY OF INVENTION

Technical Problem

An object of the present invention is to provide an observation device that enables cells cultured inside the wells of a microplate to be observed easily and clearly regardless of the height or curvature state of the liquid surface of the culturing liquid.

Solution to Problem

An aspect of the present invention provides an observation device that includes an illumination optical system that irradiates a transparent sample with illumination light from a light source, an objective lens that collects observation light from the sample, a detection optical system that detects the observation light collected by the objective lens, and a retroreflective member that is arranged opposite the objective lens with the sample interposed therebetween and in which a plurality of very small reflective elements are arrayed. The objective lens and the illumination optical system are arranged below the sample in the direction of gravity.

In the above-described aspect, the illumination optical system may be a dark-field illumination optical system that irradiates the sample with the illumination light without the illumination light passing through the objective lens.

In the above-described aspect, the illumination optical system may be an excitation illumination optical system that causes fluorescence to be generated by irradiating the sample with the illumination light without the illumination light passing through the objective lens.

In the above-described aspect, the illumination optical system may irradiate the sample with the illumination light via the objective lens.

In the above-described aspect, the illumination optical system may include an aperture that is arranged at a position that is optically conjugate with the pupil position of the objective lens, and the detection optical system may include a phase film that is arranged at the pupil position of the objective lens or at a position that is optically conjugate with the pupil position of the objective lens and has a shape that corresponds to the shape of the aperture.

In the above-described aspect, the illumination optical system may include a polarizer, the observation device may further include a birefringent element that is close to the pupil position of the objective lens, and that allows the illumination light that has been transmitted through the polarizer to be transmitted therethrough and allows the observation light from the sample that has been collected by the objective lens to be transmitted therethrough, and the detection optical system may include an analyzer that allows the observation light from the sample that has been transmitted through the birefringent element to be transmitted therethrough.

In the above-described aspect, the illumination optical system may include an aperture that is arranged at a position that is optically conjugate with the pupil position of the objective lens and may irradiate the sample with the illumination light at a specific angle.

In the above-described aspect, the detection optical system may include a light-reducing member close to a position that is optically conjugate with the pupil position of the objective lens.

In the above-described aspect, the illumination optical system may cause fluorescence to be generated by irradiating the sample with the illumination light.

The observation device according to the above-described aspect may further include a confocal disk that is arranged at a position that is optically conjugate with the focal position of the objective lens and includes a plurality of pinholes that allow the illumination light and the observation light to be transmitted therethrough.

In the above-described aspect, the illumination light may be laser light, the illumination optical system may include a scanner that causes the laser light to be scanned over the sample via the objective lens, and the detection optical system may include a pinhole that is arranged at a position that is optically conjugate with the focal position of the objective lens and allows the fluorescence that has been generated at a scanning position of the laser light in the sample and has returned via the objective lens and the scanner to pass therethrough.

The observation device according to the above-described aspect may include an optical filter that is arranged between the sample and the retroreflective member and blocks the fluorescence generated in the sample.

In the above-described aspect, the illumination light may be ultrashort-pulse laser light, and the illumination optical system may include a scanner that causes the ultrashort-pulse laser light to be scanned over the sample via the objective lens.

In the above-described aspect, the illumination light may be ultrashort-pulse laser light, and the illumination optical system may include a scanner that causes the ultrashort-pulse laser light to be scanned over the sample via the objective lens, and the illumination optical system may cause a higher harmonic to be generated at a scanning position of the ultrashort-pulse laser light in the sample.

DESCRIPTION OF EMBODIMENTS

Figure 1:
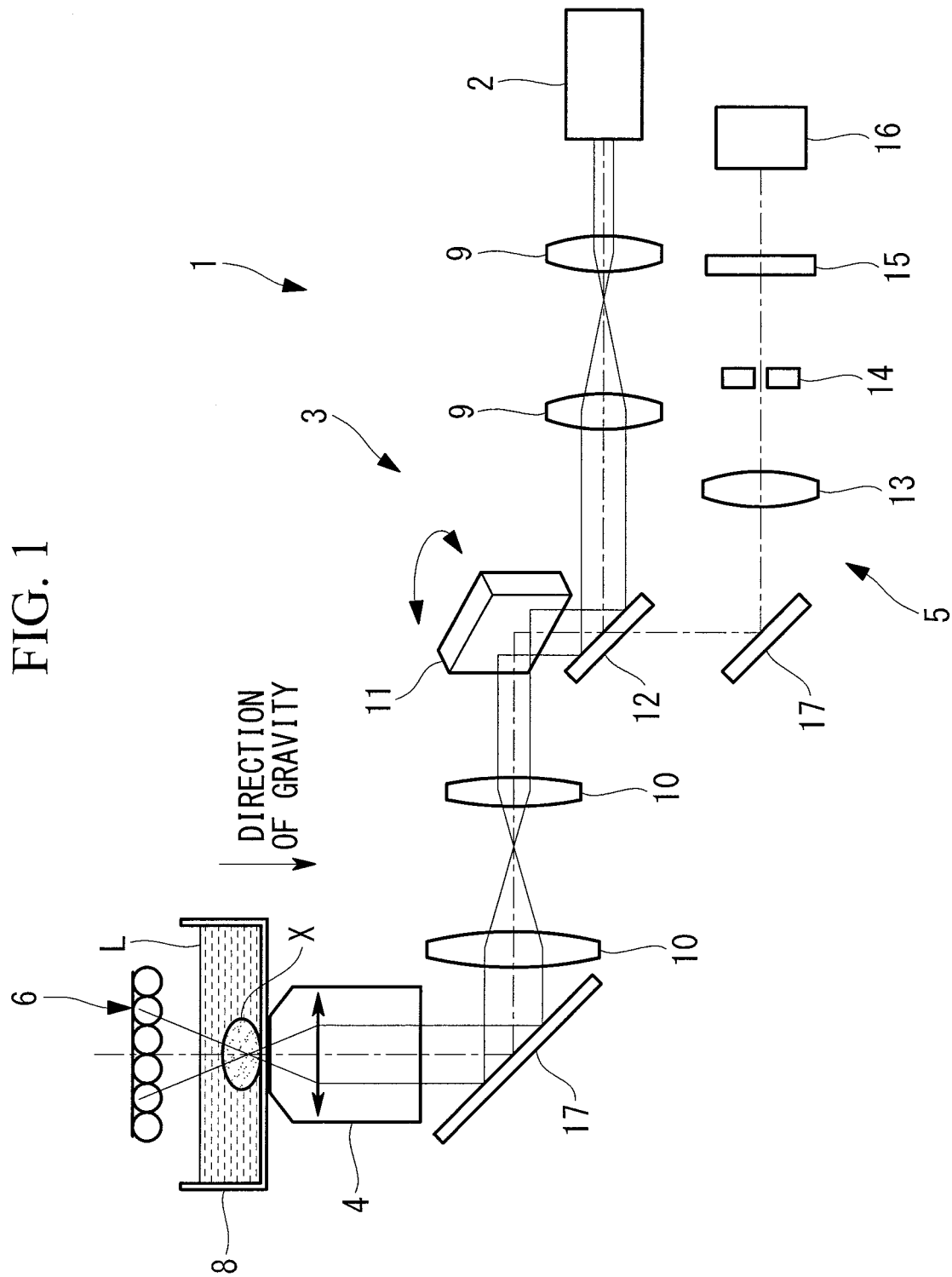
FIG. 1 is a diagram schematically illustrating an observation device according to an embodiment of the present invention.

Hereafter, an observation device 1 according to an embodiment of the present invention will be described while referring to the drawings.

As illustrated in FIG. 1, the observation device 1 according to this embodiment is a laser-scanning-type confocal fluorescence microscope, and includes an illumination optical system 3 that irradiates a sample X with laser light (illumination light) from a light source 2, an objective lens 4 that collects fluorescence (observation light) generated in the sample X, a detection optical system 5 that detects the collected fluorescence, and a retroreflective member 6 that is arranged opposite the objective lens 4 with the sample X interposed therebetween.

The sample X is for example a transparent cell that is accommodated together with a culturing liquid L inside a culture vessel 8 such as a microplate having a large number of wells.

The illumination optical system 3 includes: two relay optical systems 9 and 10 that are arranged below the culture vessel 8 in the direction of gravity and that relay laser light from the light source 2; and a scanner 11 that is arranged between the relay optical systems 9 and 10 and is composed of a galvanometer mirror that two-dimensionally scans the laser light. The laser light from the light source 2 is relayed by the relay optical systems 9 and 10 and is two-dimensionally scanned by the scanner 11, and then the laser light is collected by the objective lens 4, is radiated from below onto the sample X accommodated inside the culture vessel 8, and forms a light spot inside the sample X.

The objective lens 4 is arranged below the culture vessel 8 in the direction of gravity.

The detection optical system 5 includes: a dichroic mirror 12 that splits fluorescence from the sample X, which was collected by the objective lens 4 and returned via the relay optical system 10 and the scanner 11, off from the optical path of the laser light; an image-forming lens 13 that collects the split-off fluorescence; a confocal pinhole (pinhole) 14 that allows the imaged fluorescence to be transmitted therethrough; an excitation-light cutting filter 15 that blocks laser light included in the fluorescence; and an optical detector 16 such as a photomultiplier tube. In the figure, reference symbol 17 denotes a mirror that reflects laser light and fluorescence.

Figure 2:
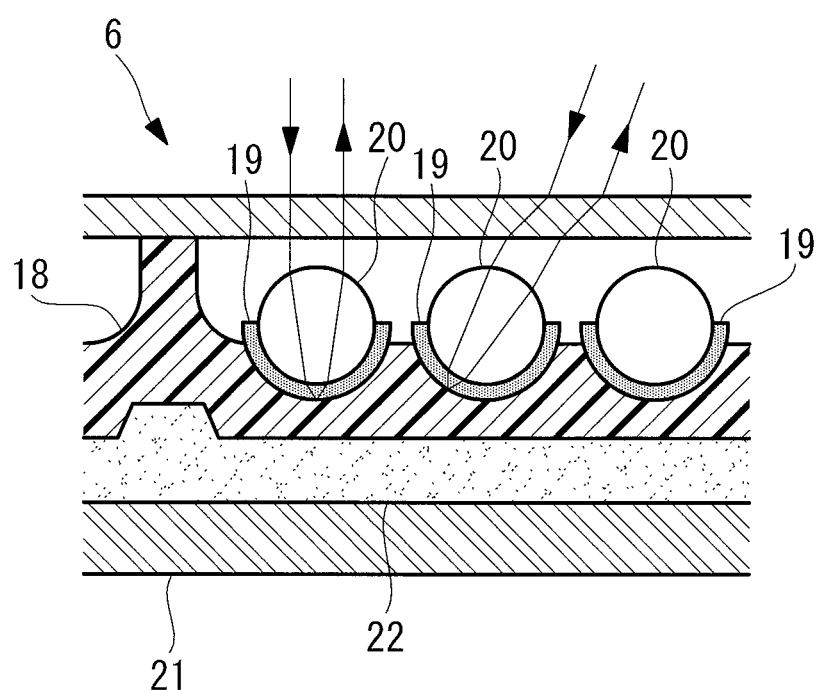
FIG. 2 is a vertical sectional view illustrating an example of a retroreflective member used in the observation device in FIG. 1.

As illustrated in FIG. 2, for example, the retroreflective member 6 is configured such that a large number of very small reflective elements 20 such as spherical glass beads or prisms are arrayed on a surface of a base member 18 with reflective films 19 interposed between the surface of the base member 18 and the reflective elements 20. Due to this configuration, light incident on the reflective elements 20 is reflected by the reflective films 19 and is emitted in the same direction as the incident direction. In this case, since the reflective elements 20 are formed so as to be very small, incident light is reflected in exactly the same direction as the incident direction with hardly any occurrence of shifting. In the figure, reference symbol 21 denotes a release film, and reference symbol 22 denotes an adhesive that adheres the release film 21 and the base member 18 to each other.

Operation of the thus-configured observation device 1 according to this embodiment will be described.

Figure 3:
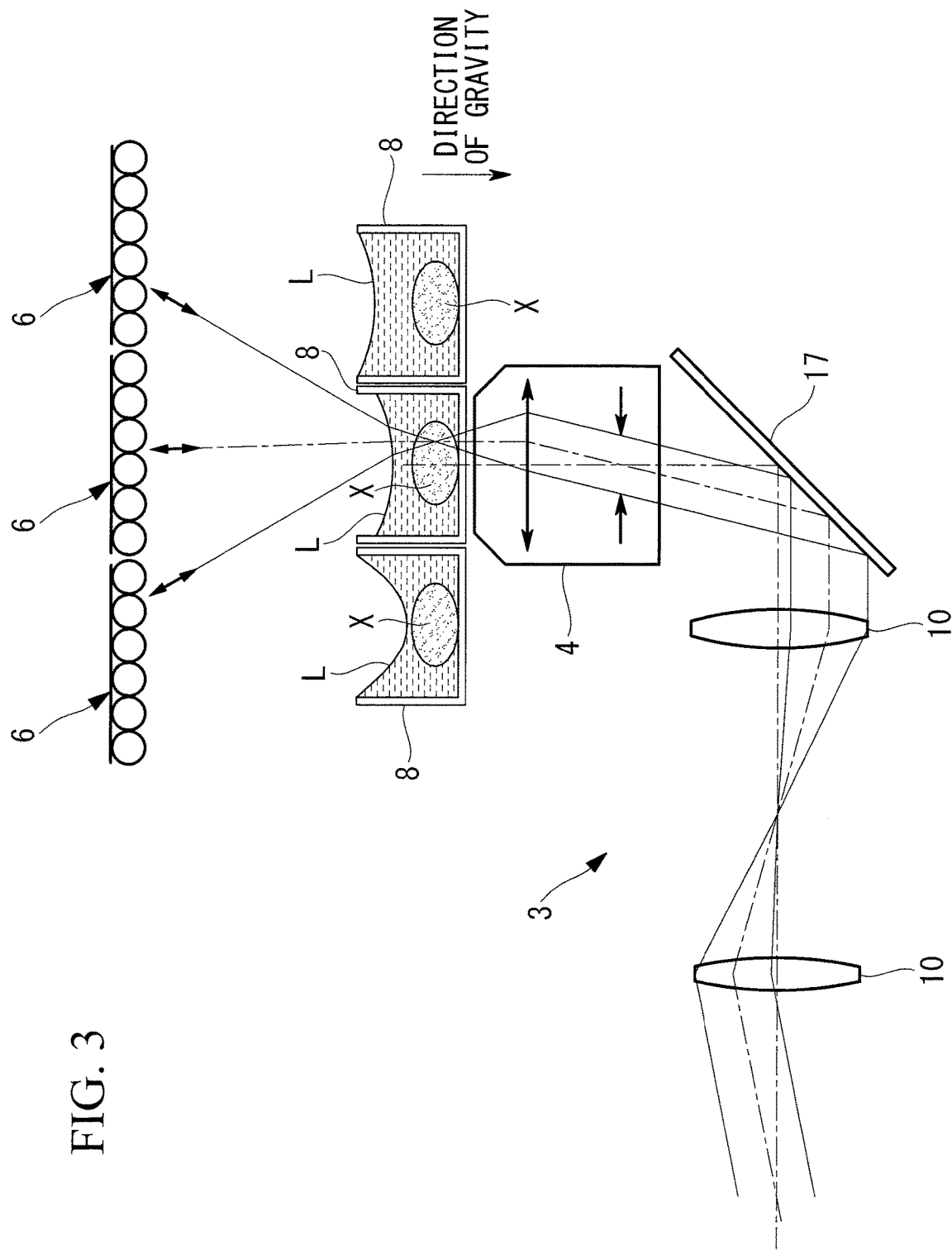
FIG. 3 is a diagram for explaining operation of the observation device in FIG. 1.

In order to observe the transparent sample X such as a cell inside the culture vessel 8 using the observation device 1 according to this embodiment, as illustrated in FIG. 3, laser light from the light source 2 is made incident on the sample X from below the culture vessel 8 by the illumination optical system 3 and the objective lens 4, a light spot is focused inside the sample X, and the light spot is two-dimensionally scanned by the scanner 11 of the illumination optical system 3.

A fluorescent material contained inside the sample X is excited and fluorescence is generated at each scanning position of the light spot of the laser light, and the generated fluorescence is emitted in all directions from each scanning position. Part of the fluorescence emitted downward from each scanning position in the sample X is transmitted through the culture vessel 8, is collected by the objective lens 4, is split off by the dichroic mirror 12 while returning along the optical path of the laser light via the scanner 11, and is detected by the optical detector 16 after passing through the image-forming lens 13, the confocal pinhole 14, and the excitation-light cutting filter 15.

In the observation device 1 according to this embodiment, since the sample X is transparent, part of the laser light that incident on the sample X from below is transmitted unaltered through the sample X and emitted upward. The laser light that is emitted upward is reflected by the retroreflective member 6 arranged above the culture vessel 8, retraces the same path, and is incident on the sample X a second time from above.

In this case, the laser light is reflected by the large number of very small reflective elements 20 of the retroreflective member 6 so as to return along the same paths with hardly any occurrence of path shifting. Thus, the light spot of the laser light can be formed a second time at substantially the same position as the initial scanning position regardless of the state of the liquid surface inside the culture vessel 8 such as the height of the liquid surface or the curvature of the liquid surface.

In other words, with the observation device 1 according to this embodiment, the laser light is reciprocatively radiated two times onto the same scanning position, and therefore the fluorescence generated at each scanning position is increased substantially twofold. Thus, there is an advantage that a bright fluorescence image can be obtained.

In the observation device 1 according to this embodiment, the objective lens 4 and the illumination optical system 3 are arranged below the culture vessel 8, in which the sample X is accommodated, in the direction of gravity, and therefore the problem of a lens effect being generated as a result of the liquid surface of the culturing liquid inside the culture vessel 8 being curved due to surface tension can be prevented.

The observation device 1 according to this embodiment is a laser-scanning-type confocal fluorescence microscope, and therefore fluorescence is generated over the entire region inside the sample X through which the laser light passes, but fluorescence generated in a region outside the light spot formed at the focal position of the objective lens 4 cannot pass through the confocal pinhole 14 and therefore is not detected by the optical detector 16.

Figure 4:
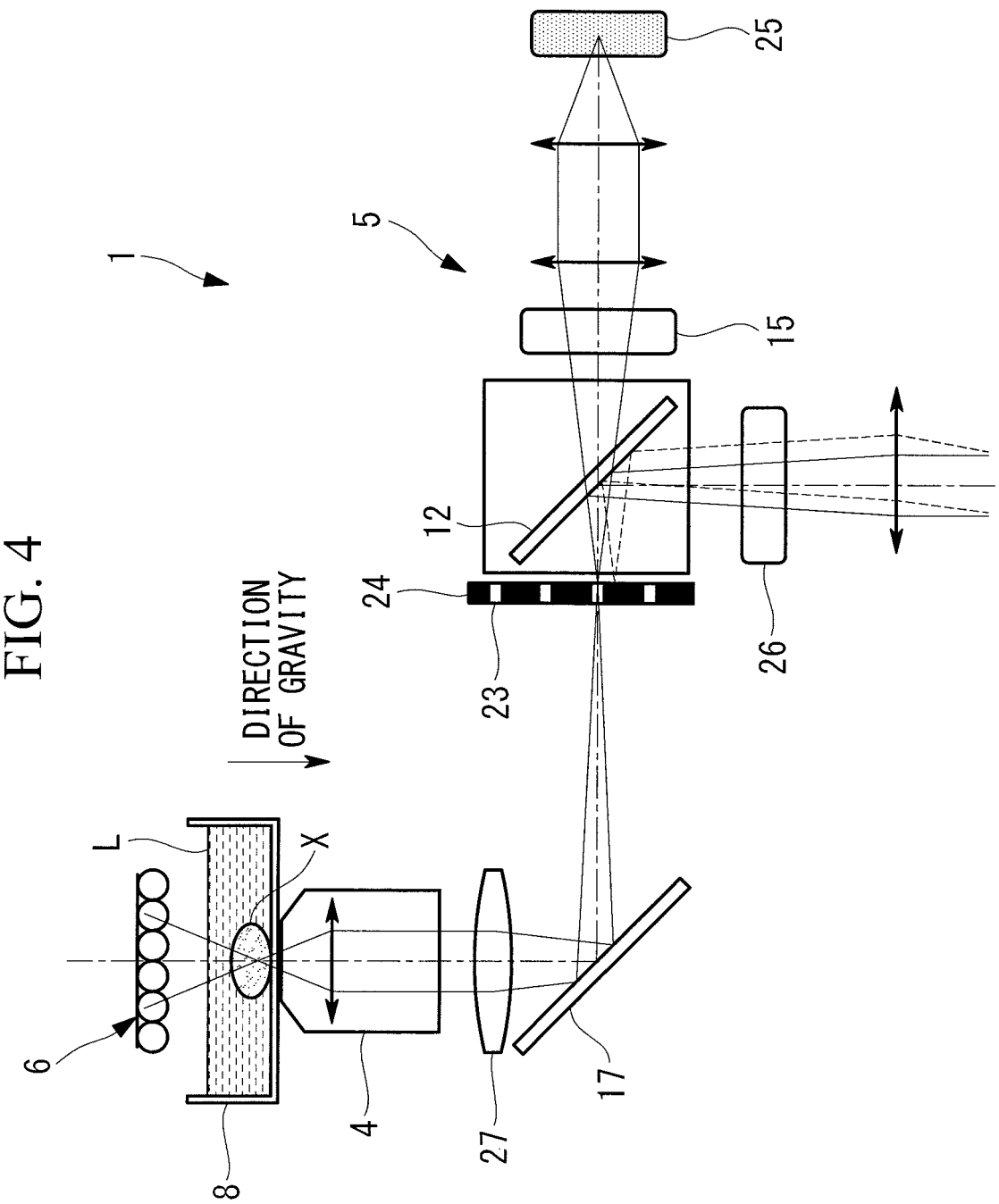
FIG. 4 is a diagram schematically illustrating a first modification of the observation device in FIG. 1.

Although a laser-scanning-type confocal fluorescence microscope that includes the scanner 11, which is composed of a galvanometer mirror, and the confocal pinhole 14 is exemplified in this embodiment, alternatively, as illustrated in FIG. 4, a configuration may instead be adopted that includes a confocal disk 24 that is arranged at a position that is optically conjugate with the focal position of the objective lens 4 and that includes a plurality of pinholes 23 that allow excitation light and fluorescence to be transmitted therethrough, and in which the detection optical system 5 includes an imaging element 25 such as a CCD that can simultaneously detect fluorescence that has passed through the plurality of pinholes 23.

Excitation light is generated by an excitation filter 26 from illumination light from the light source 2, the generated excitation light is caused to pass through the confocal disk 24 and is collected by a light-collecting lens 27, and as a result, a large number of light spots are formed at the focal position of the objective lens 4 arranged inside the sample X. The large number of light spots can be scanned inside the sample X by for example rotating the confocal disk 24.

The fluorescence generated at each scanning position passes through a pinhole 23 of the confocal disk 24 and is then split off from the optical path of the excitation light by the dichroic mirror 12. The excitation light is blocked by the excitation-light cutting filter 15 and then the fluorescence is captured by the imaging element 25.

In this case as well, the excitation light can be radiated onto the position of each light spot a second time by the retroreflective member 6, and the fluorescence generated at the position of each light spot is also reflected by the retroreflective member 6 and as a result is detected as part of the fluorescence generated from the light spot. Therefore, there is an advantage that a bright fluorescence image can be obtained.

Figure 5:
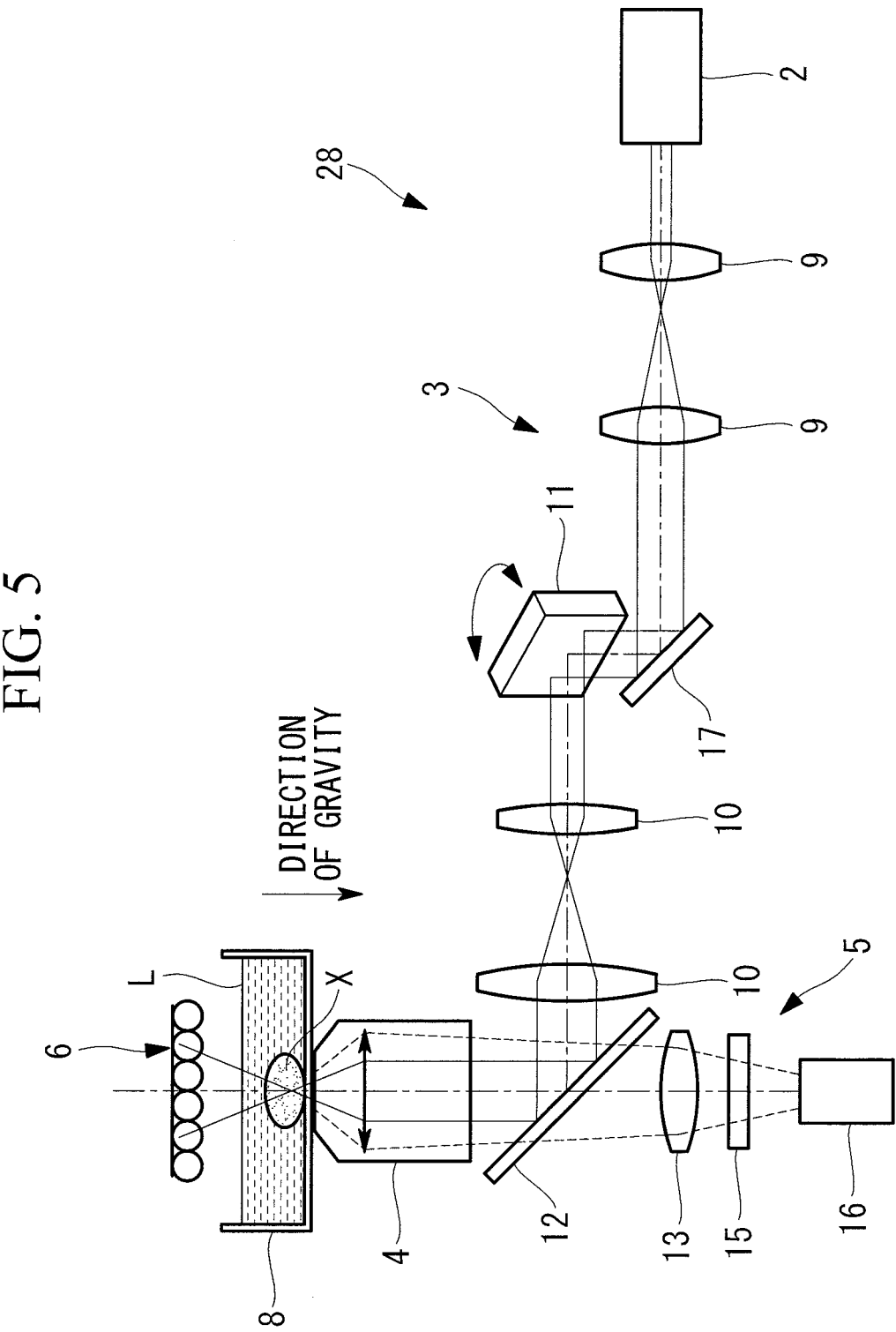
FIG. 5 is a diagram schematically illustrating a second modification of the observation device in FIG. 1.

In this embodiment, as illustrated in FIG. 5, a multi-photon-excitation type microscope may be employed in which emission of ultrashort-pulse laser light is used as the light source 2.

An observation device 28 in FIG. 5 differs from the observation device 1 in FIG. 1 in that the dichroic mirror 12 of the detection optical system 5 is arranged immediately next to the objective lens 4 and the confocal pinhole 14 is omitted.

The ultrashort-pulse laser light from the light source 2 is scanned by the scanner 11 and collected at the focal position of the objective lens 4, and as a result the photon density at the focal position is increased and fluorescence is exclusively generated at the position of the light spot due to a multi-photon excitation effect. Out of the generated fluorescence, the fluorescence that is emitted toward the objective lens 4 is collected by the objective lens 4 and is then split off from the optical path of the ultrashort-pulse laser light by the dichroic mirror 12, a laser light component is then removed by the excitation-light cutting filter 15 and the fluorescence is detected by the optical detector 16. Thus, a fluorescence image can be obtained.

Although the ultrashort-pulse laser light is reflected by the retroreflective member 6 similarly to as in the laser-scanning-type confocal fluorescence microscope, the pulse width is increased, as a result of the wavefront being divided and reflected, at the position of the light spot incident a second time inside the sample X, and therefore the multi-photon excitation effect is not generated. Therefore, in contrast to the laser-scanning-type confocal fluorescence microscope, an effect of the amount of fluorescence being amplified due to the excitation light being radiated two times is not obtained. However, fluorescence is exclusively generated at the position of the light spot and therefore flare is not generated even when a very small shift occurs due to the reflective elements 20. Therefore, the fluorescence emitted toward to the retroreflective member 6 is returned to the same position in the sample X by the retroreflective member 6 and can be collected by the objective lens 4, and fluorescence that would be lost in a conventional upright-illumination-type microscope is recovered, and consequently there is an advantage that a bright fluorescence image can be obtained.

Using a configuration similar to that in FIG. 5, an observation device 28 may be employed that detects a second harmonic (SHG) and a third harmonic (THG) induced in the sample X by incident ultrashort-pulse laser light instead of fluorescence generated by the multi-photon excitation effect.

In this case, it is sufficient that a light source that radiates ultrashort-pulse laser light with a wavelength of for example 1200 nm be employed as the light source 2, and it is sufficient that an excitation-light cutting filter that blocks ultrashort-pulse laser light with a wavelength of 1200 nm and transmits ultrashort-pulse laser light with wavelengths of 600 nm and 400 nm be employed as the excitation-light cutting filter 15.

A transparent cell can be detected without the use of fluorescent labeling by detecting harmonics generated by a non-linear effect resulting from a specific substance inside the sample X. There is an advantage in that, usually, a large proportion of each generated harmonic is returned toward the sample X by the retroreflective member 6 in a direction so as to be transmitted toward the opposite side with respect to the incidence direction of the ultrashort-pulse laser light and can be detected using a compact upright-illumination-type configuration.

Figure 6:
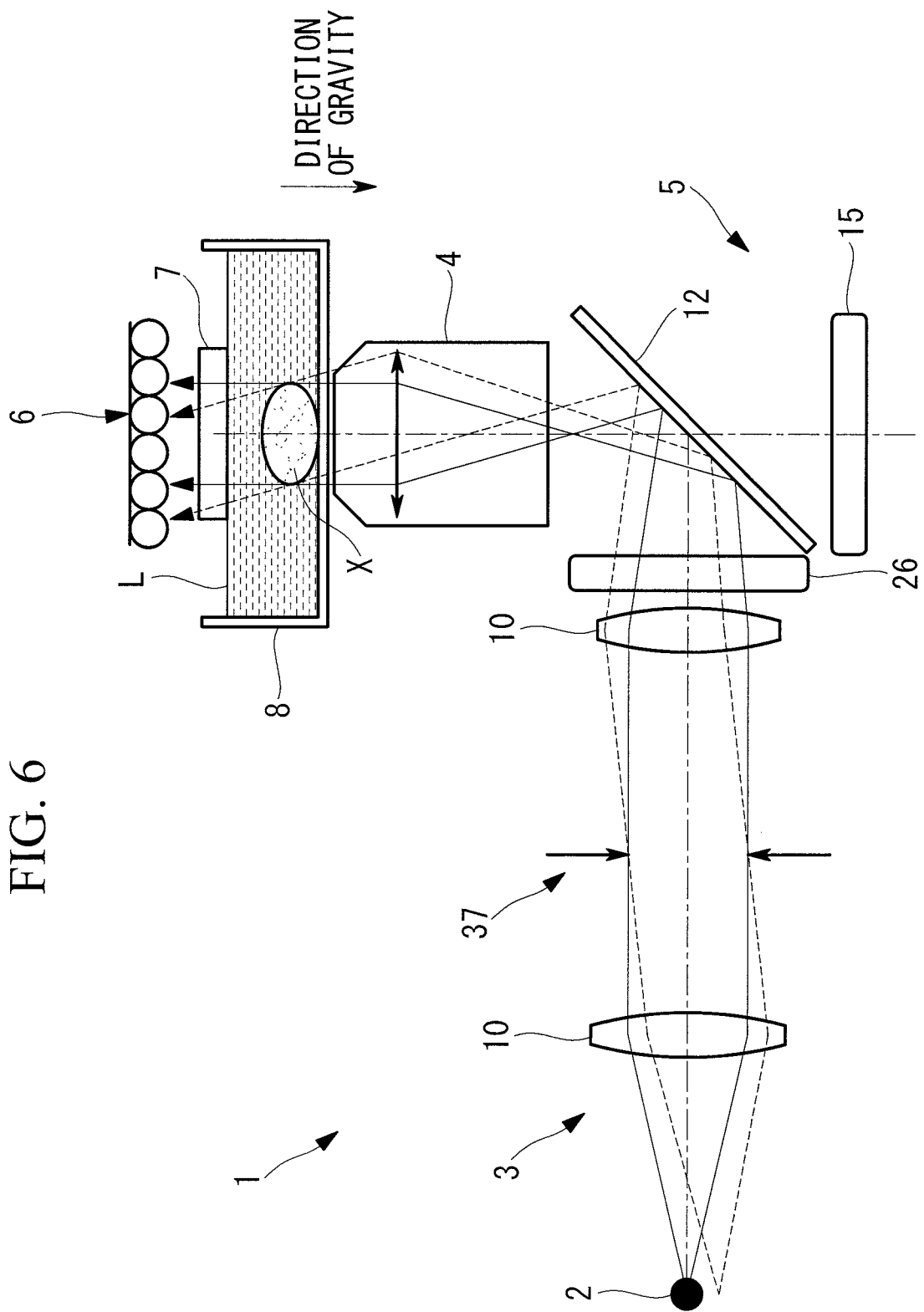
FIG. 6 is a diagram schematically illustrating a third modification of the observation device in FIG. 1.

Although a scanning-type fluorescence microscope and so forth have been described in this embodiment, alternatively, as illustrated in FIG. 6, the present invention may be applied to a microscope in which excitation light from the light source 2 is radiated over the entire sample X using the objective lens 4 (wide field illumination), fluorescence generated at the individual positions in the sample X is collected by the objective lens 4, excitation light is removed, the fluorescence is captured, and thereby a fluorescence image is obtained. In the figure, reference symbol 37 denotes an aperture.

In this case, the observation device 1 includes an optical filter 7 that is arranged next to the retroreflective member 6 and blocks fluorescence.

The optical filter 7 is configured to block fluorescence emitted toward the retroreflective member 6 out of fluorescence generated in the sample X by radiation of laser light.

In the case where the sample X exhibits strong scattering, fluorescence generated in the sample X is emitted toward the retroreflective member 6 and fluorescence reflected by the retroreflective member 6 is scattered a second time in the sample X, and the contrast may be lowered. The optical filter 7 is arranged between the retroreflective member 6 and the sample X, and consequently fluorescence emitted toward the retroreflective member 6 is blocked by the optical filter 7 and only excitation light is transmitted through the optical filter 7, and the excitation light reflected by the retroreflective member 6 is incident a second time on the sample X. Thus, fluorescence intensity can be doubled while preventing a reduction in contrast.

Specifically, the excitation light that has been transmitted through the individual positions in the sample X is reflected by the retroreflective member 6 and is incident a second time on the same positions in the sample X, and therefore, approximately twice the fluorescence can be generated at the individual positions in the sample X.

Thus, a bright fluorescence image can be obtained.

In this case, when the light source 2 is not a point light source (for example, a mercury light source), not only on-axis excitation light, but also off-axis excitation light is radiated onto the sample X. According to the observation device 1 of this embodiment, since not only on-axis excitation light but also off-axis excitation light are reflected by the retroreflective member 6 and caused to return along the same path, the above-described effect can be obtained (refer to dotted light beams in FIG. 6).

A configuration similar to that in this embodiment may be applied to an upright-illumination-type differential interference microscope.

Figure 7:
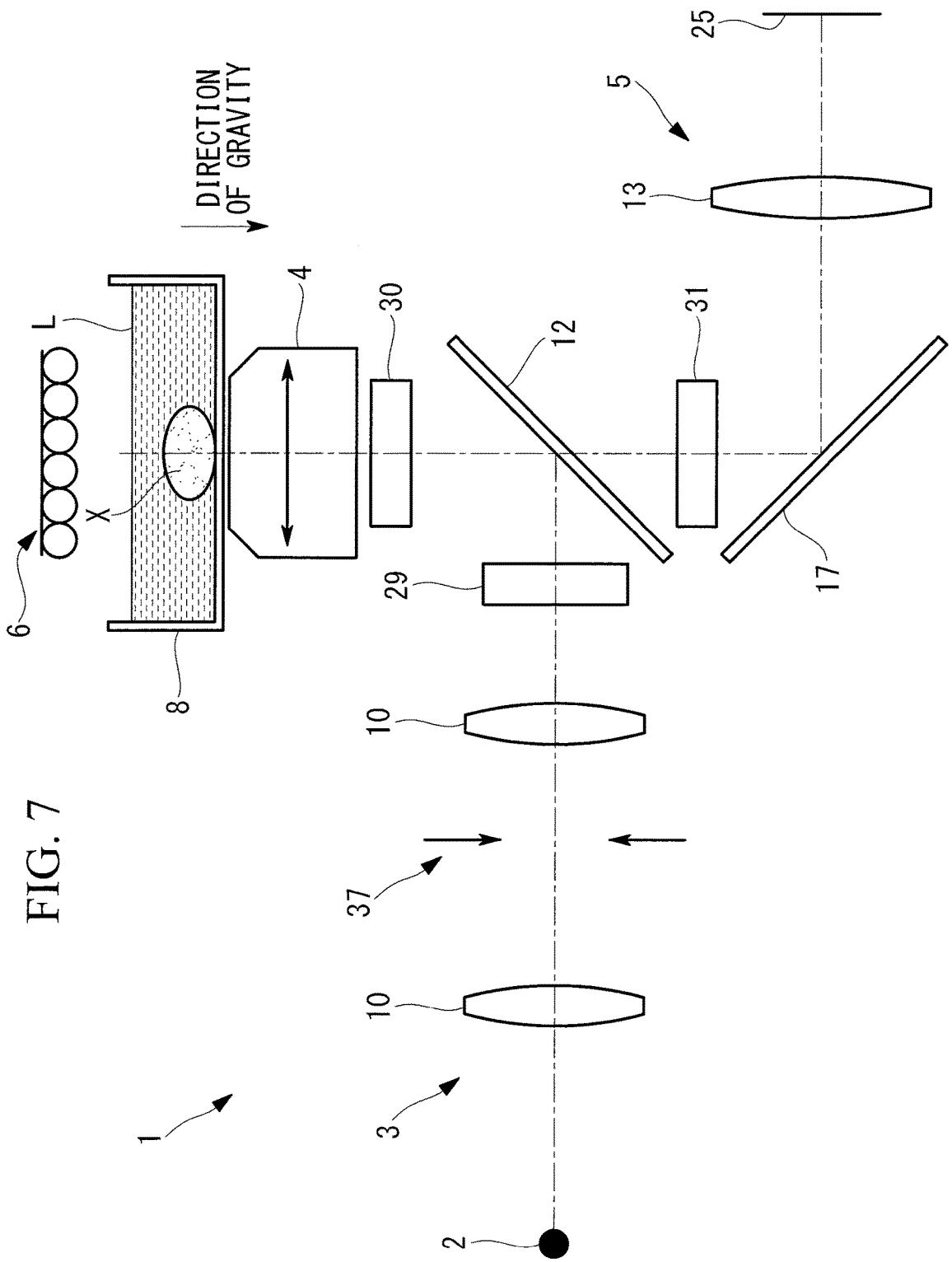
FIG. 7 is a diagram schematically illustrating a fourth modification of the observation device in FIG. 1.

In this case, as illustrated in FIG. 7, it is sufficient that the illumination optical system 3 include a polarizer 29 that allows illumination light from the light source 2 to pass therethrough, that the observation device 1 include, close to the pupil position of the objective lens 4, a birefringent element 30 that allows illumination light that has been transmitted through the polarizer 29 to be transmitted therethrough and that allows observation light from the sample X that has been collected by the objective lens 4 to be transmitted therethrough, and that the detection optical system 5 include an analyzer 31 that allows observation light from the sample X that has been transmitted through the birefringent element 30 to be transmitted therethrough.

With this configuration, the polarization direction of the illumination light is set to one direction by making the illumination light be transmitted through the polarizer 29, the illumination light is then split into two illumination light beams having different polarization directions by causing the illumination light to be transmitted through the birefringent element 30, and the illumination light beams are then caused to be transmitted through the sample X. An optical path difference is imparted to two illumination light beams having different optical paths when the illumination light beams are transmitted through parts of the sample X where the thickness changes, and after being reflected by the retroreflective member 6, the illumination light beams are caused to be transmitted through the same positions in the sample X a second time and are imparted with an optical path difference a second time.

Then, the illumination light beams are caused to pass through the birefringent element 30 a second time and are combined with each other along the same optical path, and the illumination light is then caused to pass through the analyzer 31. Thus, brightness contrast is generated through interference when there is an optical path difference between the two illumination light beams and the sample X can be observed using a differential interference image.

In this case as well, the illumination light that has been transmitted through the individual positions in the sample X is caused to pass through the same positions in the sample X a second time by the retroreflective member 6, and as a result the phase difference generated through birefringence can be doubled.

A configuration similar to that in this embodiment may be applied to a phase contrast microscope.

Figure 8:
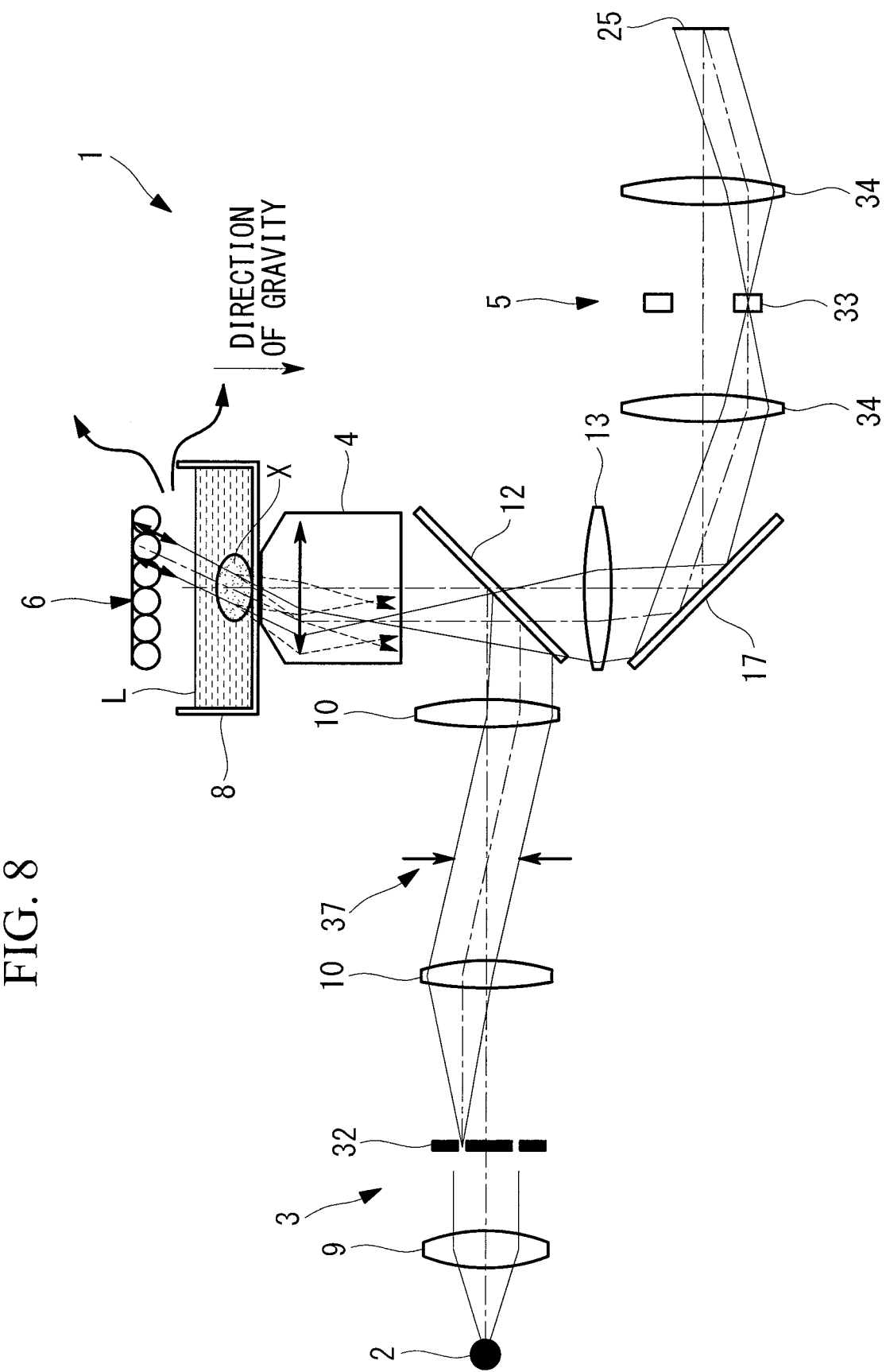
FIG. 8 is a diagram schematically illustrating a fifth modification of the observation device in FIG. 1.

In this case, as illustrated in FIG. 8, it is sufficient that the illumination optical system 3 include a ring slit (aperture) 32 that is arranged at a position that is optically conjugate with the pupil position of the objective lens 4, and that the detection optical system 5 include a phase film 33, which has an O-ring plate-like shape corresponding to the shape of the ring slit 32, that is arranged at the pupil position of the objective lens 4 or at a position that is optically conjugate with the pupil position of the objective lens 4. In the figure, reference symbol 34 denotes a relay optical system.

With this configuration, phase difference observation can be performed using a compact upright-illumination-type configuration. In other words, illumination light from the light source 2 that has passed through the ring slit 32, which is arranged at a position that is optically conjugate with the pupil position of the objective lens 4, is transmitted through the sample X, is then reflected by the retroreflective member 6, is returned along the same direction, is radiated onto the sample X once again, and is diffracted by the sample X. Illumination light that propagates in a forward direction through the sample X without being diffracted is phase shifted as a result of being caused to pass through the phase film 33. Then, the phase-shifted forward-propagating light and the diffracted light are made to interfere with each other, and the transparent sample X can be observed on the basis of the brightness thereof.

In this case, although diffraction also occurs in the sample X when the light is radiated from diagonally below the sample X, so long as the transmittance of the sample X is high and reflectance of the retroreflective member 6 is sufficiently high, the resulting noise is of such a degree that the noise can be ignored.

A configuration similar to that in this embodiment may be applied to transmission observation using oblique illumination.

Figure 9:
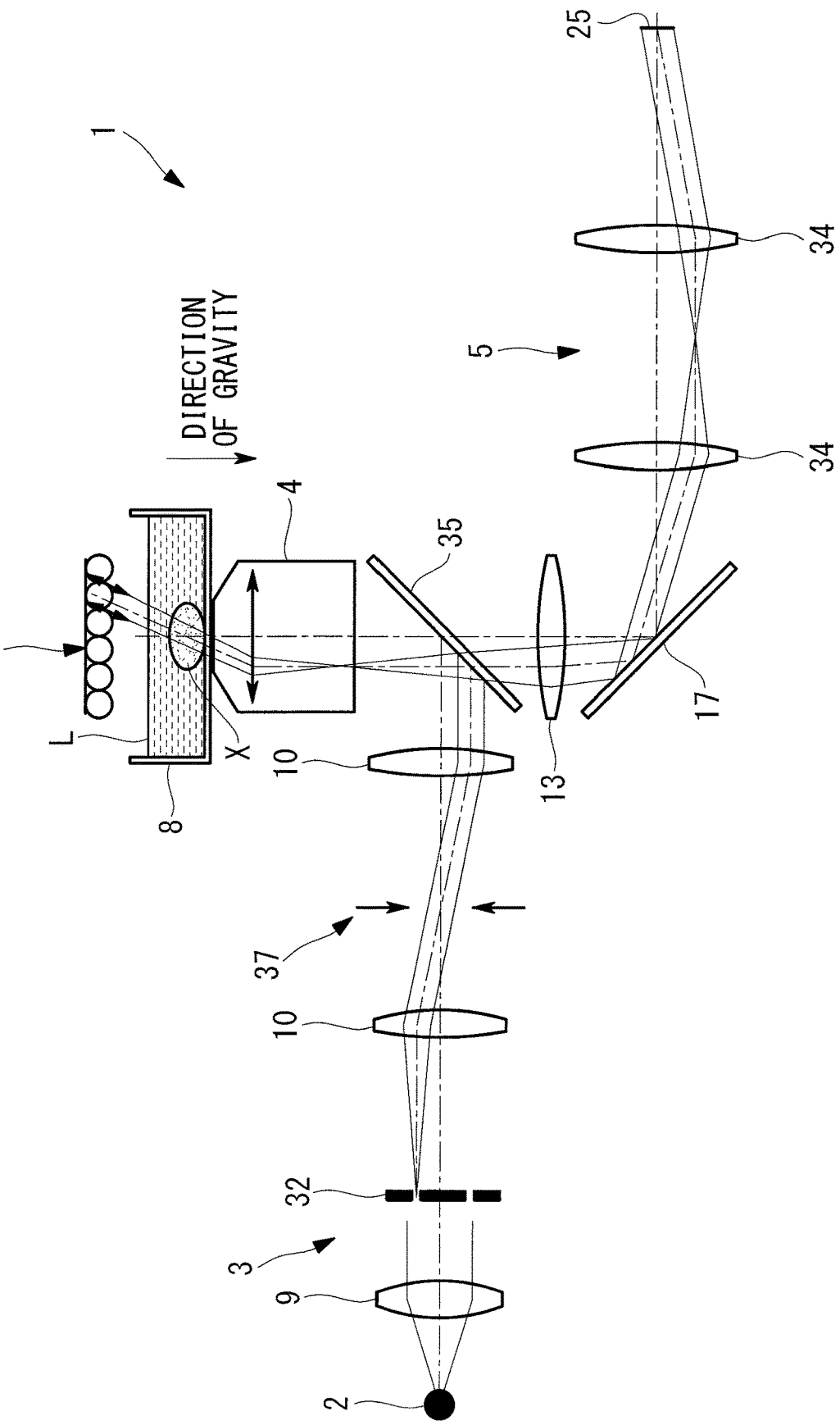
FIG. 9 is a diagram schematically illustrating a sixth modification of the observation device in FIG. 1.

In this case, as illustrated in FIG. 9, the illumination optical system 3 may include a ring slit (aperture) 32 that is arranged at a position that is spaced apart from an optical axis center in a radial direction at a position that is optically conjugate with the pupil position of the objective lens 4, and may cause illumination light to be incident on the sample X at a specific angle.

With this configuration, illumination light that has been caused to be transmitted through the sample X from diagonally below is reflected by the retroreflective member 6 and as a result oblique illumination is generated that is incident on the sample from diagonally above, the transmitted observation light is split by a half mirror 35 and then captured by the imaging element 25 such as a CCD, and as a result the sample X can be observed using image that has a stereoscopic quality.

Figure 10:
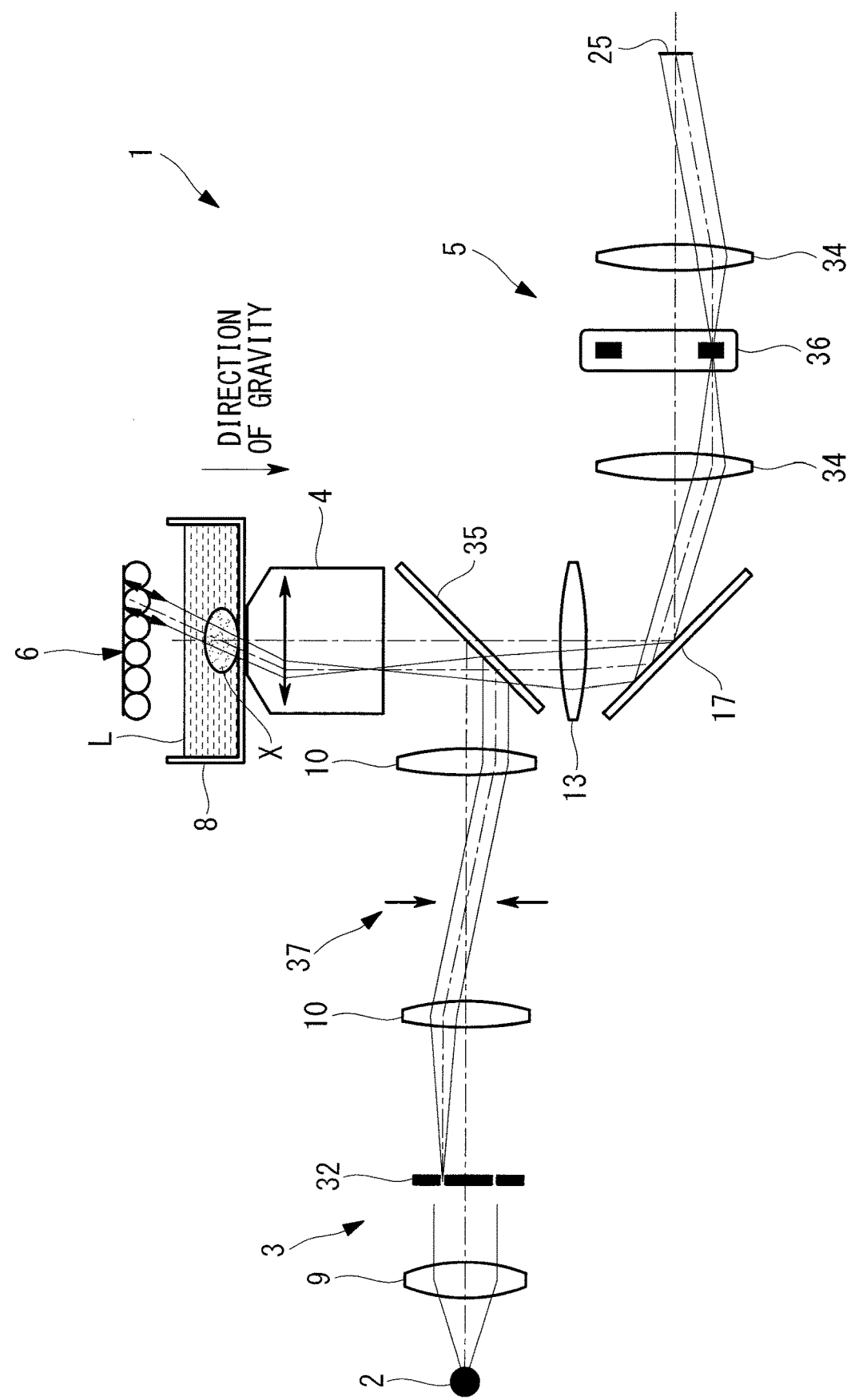
FIG. 10 is a diagram schematically illustrating a seventh modification of the observation device in FIG. 1.

As illustrated in FIG. 10, the detection optical system 5 may include a light-reducing member 36 at a position that corresponds to the ring slit 32 in the vicinity of a position that is optically conjugate with the pupil position of the objective lens 4. With this configuration, the amount of direct light that passes through the sample X from the retroreflective member 6 as oblique illumination can be reduced by the light-reducing member 36, and as a result dark-field observation can be performed.

Figure 11:
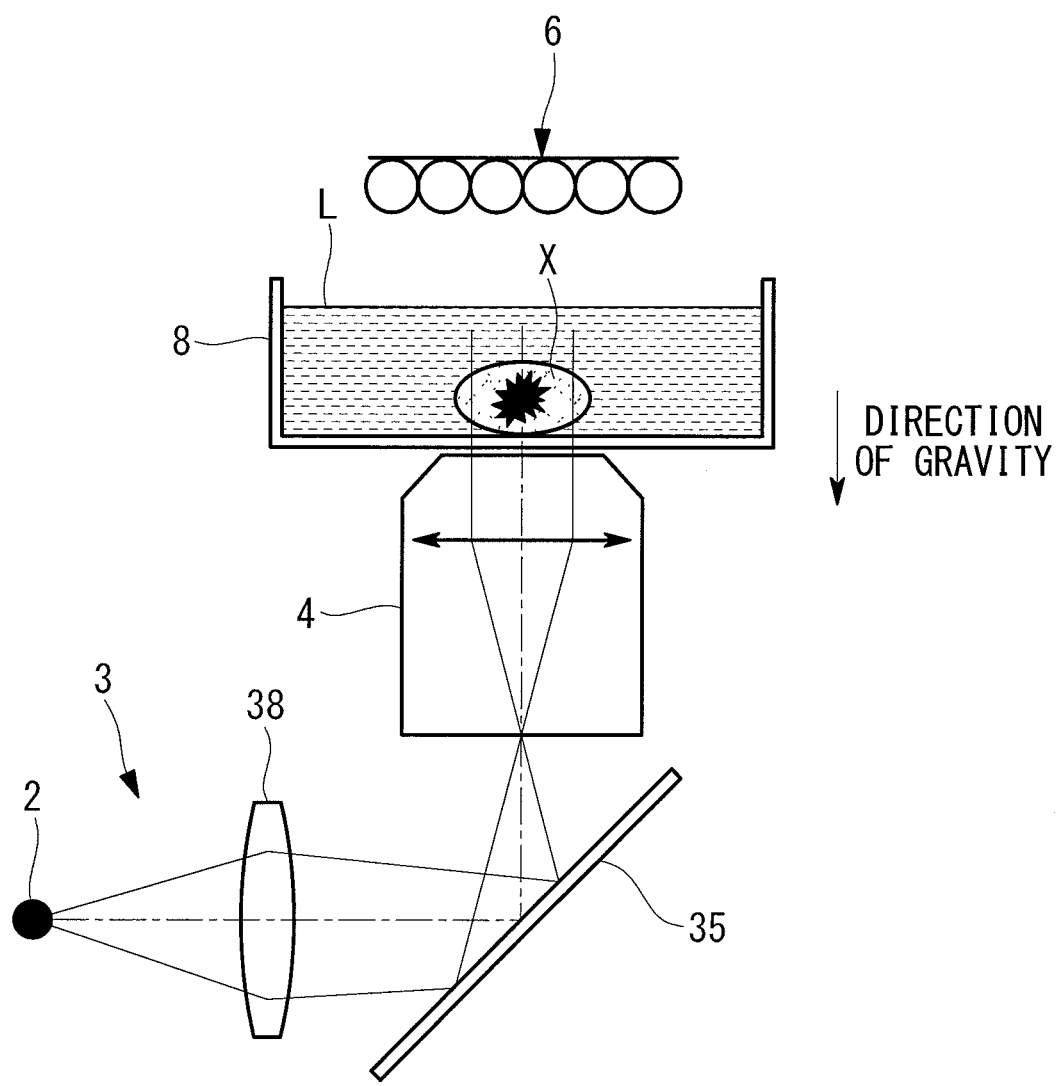
FIG. 11 is a diagram schematically illustrating an eighth modification of the observation device in FIG. 1.

As illustrated in FIG. 11, a bright-field observation microscope that has a configuration similar to that in this embodiment may be adopted. In the figure, reference symbol 38 denotes a light-collecting lens.

In the case where the transmittance of the sample X is low, part of the illumination light is reflected by the sample X and the rest of the illumination light is transmitted through the sample X. Part of the illumination light that has been radiated onto the sample X from below by the objective lens 4 is reflected by the sample X and collected by the objective lens 4, and illumination light that has been transmitted through the sample X is reflected by the retroreflective member 6, is radiated a second time onto the sample X, and is collected by the objective lens 4 as transmitted light. Thus, upright-illumination bright-field observation and transmission bright-field observation can be simultaneously performed using an upright-illumination-type configuration. There is an advantage in that observation can be performed using a bright-field image that changes depending on the transmittance of the sample X.

Figure 12:
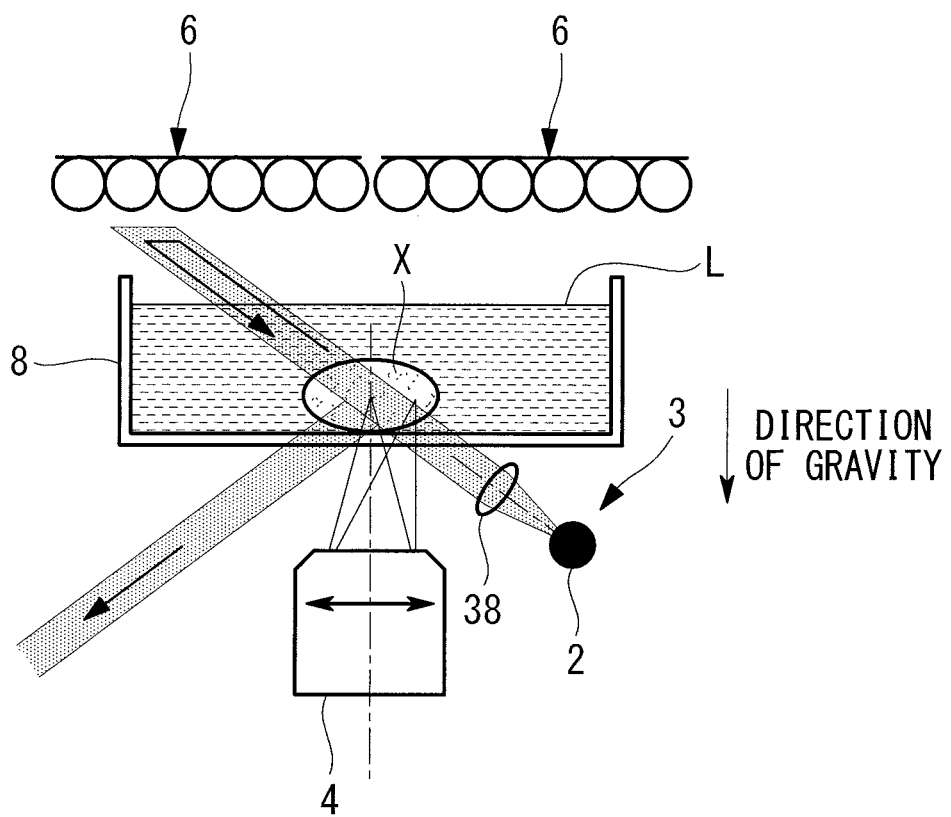
FIG. 12 is a diagram schematically illustrating a ninth modification of the observation device in FIG. 1.

In the above-described embodiment, a case is described in which the sample X is irradiated with illumination light via the objective lens 4, but alternatively, as illustrated in FIG. 12, the present invention may be applied to a case in which the sample X is irradiated with illumination light without the illumination light passing through the objective lens 4.

With this configuration, the sample X is irradiated with illumination light by the illumination optical system (dark-field illumination optical system) 3 without the illumination light passing through the objective lens 4, and light scattered by the sample X is collected by the objective lens 4 and detected by the detection optical system 5.

Thus, a dark-field image of the sample X can be observed. In this case, among scattering occurring in the sample X, both backward scattering of illumination light incident from the light source 2 side and forward scattering of illumination light incident from the retroreflective member 6 side are detected, and forward-scattered illumination light can be observed more brightly than backward-scattered illumination light. In other words, bright observation light resulting from forward scattering, as in the case of transmission observation, can be observed while decreasing the installation space on the opposite side of the sample X by arranging the detection optical system 5 on the same side of the sample X as the light source 2.

In the above-described embodiment, the illumination optical system 3 may be an excitation illumination optical system that causes fluorescence to be generated by irradiating the sample X with illumination light without the illumination light passing through the objective lens 4.

With this configuration, the sample X is irradiated with illumination light by the illumination optical system 3 without the illumination light passing through the objective lens 4, and fluorescence generated in the sample X is collected by the objective lens 4 and detected by the detection optical system 5.

Thus, a fluorescence image of the sample X can be observed. In this case, after the illumination light is incident on the sample X from the light source 2 side, light reflected by the retroreflective member 6 is also incident on the sample X. Thus, a bright fluorescence image can be observed.

In this embodiment, the planar retroreflective member 6 is arranged substantially horizontally above the culture vessel 8 in which the sample X is accommodated, but the present invention is not limited to this configuration. In other words, it is sufficient that the retroreflective member 6 be arranged at a position so as to allow illumination light, fluorescence or the like emitted in a direction so as to be transmitted through the sample X to be incident thereon, and the position in the height direction, the shape, the attitude, and so on of the retroreflective member 6 can be arbitrarily set.

For example, the retroreflective member 6 may be rolled up into a cylindrical form when not in use, may be spread out and arranged in a curved form at the time of use, may be folded up when not in use, or may be spread out and arranged in an uneven form at the time of use. In addition, the retroreflective member 6 may be arranged so as to be inclined with respect to a horizontal direction. In other words, since strict accuracy is not required with respect to the arrangement and shape of the retroreflective member 6, an arbitrarily shaped retroreflective member 6 may be arranged at an arbitrary position. The retroreflective member 6 may be arranged on a ceiling so as to cover an area in which illumination light or the like emitted in a direction so as to be transmitted through the sample X is incident. In this case, a light-collecting lens may be arranged above the culture vessel 8 in order to decrease the area over which the light is incident on the retroreflective member 6.

It is preferable that the reflective elements 20 of the retroreflective member 6 be formed of a non-resin material such as glass. Since most resin materials generate auto-fluorescence, it is preferable that a material that does not generate auto-fluorescence be used.

An aperture size d of a single reflective element 20 of the retroreflective member 6 preferably satisfies the following conditional expression, where λ is the wavelength of the light used and D is the aperture diameter of the part of the retroreflective member 6 irradiated simultaneously.

$$2\lambda < d < D/10$$

Thus, diffraction can be prevented when illumination light is reflected, and illumination light can be reflected in the same direction without a particularly large shift.

As a result, the following aspect is derived from the above-described embodiment.

An aspect of the present invention provides an observation device that includes: an illumination optical system that irradiates a transparent sample with illumination light from a light source; an objective lens that collects observation light from the sample; a detection optical system that detects the observation light collected by the objective lens; and a retroreflective member that is arranged opposite the objective lens with the sample interposed therebetween and in which a plurality of very small reflective elements are arrayed. The objective lens and the illumination optical system are arranged below the sample in the direction of gravity.

According to this aspect, when the sample is irradiated with illumination light emitted from the light source by the illumination optical system, at least part of the illumination light is transmitted through the sample and is incident on the retroreflective member arranged opposite the objective lens with the sample interposed therebetween. The retroreflective member is formed by arraying a plurality of very small reflective elements, and therefore light incident on the retroreflective member is reflected in exactly the same direction as the incident direction with hardly any occurrence of shifting. Thus, the illumination light is incident on the sample a second time from exactly the same direction as the emission direction of the illumination light that has been transmitted through the sample. Then, observation light from the sample is collected by the objective lens and detected by the detection optical system. Thus, the sample can be observed using the detected observation light.

In this case, since the retroreflective member reflects the light incident thereon in exactly the same direction as the incident direction with hardly any occurrence of shifting, uniform illumination light can be made incident on each well of a microplate from the retroreflective member side as well, even when there are differences between the wells in terms of the heights and refractive powers of the liquid surfaces of the culturing liquid inside the wells. Thus, cells cultured inside the wells of a microplate can be observed easily and clearly regardless of the height or curvature state of the liquid surface of the culturing liquid. In addition, since the objective lens and the illumination optical system are arranged below the sample in the direction of gravity, the problem of a lens effect being generated due to the liquid surfaces of the culturing liquid inside the wells of the microplate being curved due to surface tension can be prevented.

In the above-described aspect, the illumination optical system may be a dark-field illumination optical system that irradiates the sample with the illumination light without the illumination light passing through the objective lens.

With this configuration, the sample is irradiated with illumination light by the illumination optical system, which is composed of a dark-field illumination optical system, without the illumination light passing through the objective lens, and light scattered by the sample is collected by the objective lens and detected by the detection optical system.

Thus, a dark-field image of the sample can be observed. In this case, among scattering occurring in the sample, both backward scattering of illumination light incident from the light source side and forward scattering of illumination light incident from the retroreflective member side are detected. Forward scattering can be observed more brightly than backward scattering. In other words, bright observation light resulting from forward scattering, as in the case of transmission observation, can be observed while decreasing the installation space on the opposite side of the sample by arranging the detection optical system on the same side of the sample as the light source.

In the above-described aspect, the illumination optical system may be an excitation illumination optical system that causes fluorescence to be generated by irradiating the sample with the illumination light without the illumination light passing through the objective lens.

With this configuration, the sample is irradiated with illumination light by the illumination optical system, which is composed of an excitation illumination optical system, without the illumination light passing through the objective lens, and fluorescence generated in the sample is collected by the objective lens and detected by the detection optical system.

Thus, a fluorescence image of the sample can be observed. In this case, after the illumination light is incident on the sample from the light source side, light reflected by the retroreflective member is also incident on the sample. Thus, a bright fluorescence image can be observed.

In the above-described aspect, the illumination optical system may irradiate the sample with the illumination light via the objective lens.

With this configuration, coaxial upright-illumination observation can be performed. For example, in the case where bright-field observation is performed in which reflected light or transmitted light from the sample is observed, reflected light, which results from illumination light radiated onto the sample from the light source via the objective lens being reflected by the sample, and transmitted light, which results from illumination light that has been transmitted through the sample and reflected by the retroreflective member being transmitted through the sample, are collected by the objective lens and detected by the detection optical system. Both an upright-illumination bright-field image and a transmission bright-field image can be observed, and bright-field images that appear different depending on the transmittance of the sample can be observed.

In the above-described aspect, the illumination optical system may include an aperture that is arranged at a position that is optically conjugate with the pupil position of the objective lens, and the detection optical system may include a phase film that is arranged at the pupil position of the objective lens or at a position that is optically conjugate with the pupil position of the objective lens and has a shape that corresponds to the shape of the aperture.

With this configuration, upright-illumination phase difference observation can be performed. In other words, illumination light from the light source that has passed through the aperture, which is arranged at a position that is optically conjugate with the pupil position of the objective lens, is transmitted through the sample, is then reflected by the retroreflective member, is returned along the same direction, is radiated onto the sample once again, and is diffracted in the sample. Illumination light that propagates in a forward direction through the sample without being diffracted is phase shifted as a result of being caused to pass through the phase film. Then, the phase-shifted forward-propagating light and the diffracted light are caused to interfere with each other, and as a result the transparent sample can be observed on the basis of the brightness thereof.

In the above-described aspect, the illumination optical system may include a polarizer, and the observation device may include a birefringent element that is close to the pupil position of the objective lens, and allows illumination light that has been transmitted through the polarizer to be transmitted therethrough and allows observation light from the sample that has been collected by the objective lens to be transmitted therethrough, and the detection optical system may include an analyzer that allows the observation light from the sample that has been transmitted through the birefringent element to be transmitted therethrough.

With this configuration, the polarization direction of the illumination light is set to one direction by causing the illumination light to be transmitted through the polarizer, the illumination light is then split into two illumination light beams having different polarization directions by causing the illumination light to be transmitted through the birefringent element, and the illumination light beams are then caused to be transmitted through the sample. An optical path difference is imparted to two illumination light beams having different optical paths when the illumination light beams are transmitted through parts of the sample where the thickness changes, and after being reflected by the retroreflective member, the illumination light beams are caused to be transmitted through the same positions in the sample a second time and are imparted with an optical path difference a second time. Then, the illumination light beams are caused to pass through the birefringent element a second time and are thereby combined with each other along the same optical path, and are then caused to pass through the analyzer. As a result, brightness contrast is generated through interference when there is an optical path difference between the two illumination light beams. Thus, the sample can be observed as a differential interference image.

In the above-described aspect, the illumination optical system may include an aperture that is arranged at a position that is optically conjugate with the pupil position of the objective lens and may irradiate the sample with the illumination light at a specific angle.

With this configuration, oblique illumination of the sample can be performed and the sample can be observed as an image that has a stereoscopic quality.

In the above-described aspect, the detection optical system may include a light-reducing member close to a position that is optically conjugate with the pupil position of the objective lens.

With this configuration, the amount of direct light that passes through the aperture is reduced by the light-reducing member, and therefore dark-field observation can be performed.

In the above-described aspect, the illumination optical system may cause fluorescence to be generated by irradiating the sample with the illumination light.

With this configuration, the sample is irradiated with illumination light by the illumination optical system without the illumination light passing through the objective lens, and fluorescence generated in the sample is collected by the objective lens and detected by the detection optical system.

Thus, a fluorescence image of the sample can be observed. In this case, after the illumination light is incident on the sample from the light source side, light reflected by the retroreflective member is also incident on the sample. Thus, a bright fluorescence image can be observed.

The observation device according to above-described aspect may further include a confocal disk that is arranged at a position that is optically conjugate with the focal position of the objective lens and includes a plurality of pinholes that allow the illumination light and the observation light to be transmitted therethrough.

With this configuration, the illumination light from the light source passes through the pinholes of the confocal disk, forms a plurality of spots on the sample via the objective lens, and causes fluorescence to be generated by exciting a fluorescent substance at the positions of the spots. Among the generated fluorescence, fluorescence that has been collected by the objective lens and has passed through the pinholes of the confocal disk is captured. In this case, a two-dimensional fluorescence image can be captured by scanning the spots over the sample by for example rotating the confocal disk.

In this case, illumination light, which causes fluorescence to be generated by being incident on the sample, is transmitted through the sample and is returned by the retroreflective member, and then the illumination light is incident on the sample a second time at the same positions, and therefore fluorescence can be generated a second time and observation can be performed using a bright fluorescence image obtained by increasing the amount of detected fluorescence.

In the above-described aspect, the illumination light may be laser light, the illumination optical system may include a scanner that causes the laser light to be scanned over the sample via the objective lens, and the detection optical system may include a pinhole that is arranged at a position that is optically conjugate with the focal position of the objective lens and that allows the fluorescence that has been generated at a scanning position of the laser light in the sample and has returned via the objective lens and the scanner to pass therethrough.

With this configuration, the illumination light from the light source forms a spot on the sample via the objective lens and causes fluorescence to be generated at each position of the spot. A two-dimensional fluorescence image of the sample can be obtained by moving the spot over the sample using the scanner.

In this case, illumination light, which causes fluorescence to be generated by being incident on the sample, is transmitted through the sample and is returned by the retroreflective member, and then the illumination light is incident on the sample a second time at the same position, and therefore fluorescence can be generated a second time and observation can be performed using a bright fluorescence image obtained by increasing the amount of detected fluorescence.

The observation device according to the above-described aspect may include an optical filter that is arranged between the sample and the retroreflective member and blocks the fluorescence generated in the sample.

With this configuration, among fluorescence generated in the sample as a result of the sample being irradiated with illumination light, fluorescence that is emitted toward the retroreflective member is blocked by the optical filter and therefore the fluorescence can be prevented from being returned by the retroreflective member and being made incident on the sample a second time. Thus, a reduction in contrast caused by the detection of fluorescence scattered by the sample can be prevented.

In the above-described aspect, the illumination light may be ultrashort-pulse laser light, and the illumination optical system may include a scanner that causes the ultrashort-pulse laser light to be scanned over the sample via the objective lens.

With this configuration, the ultrashort-pulse laser light from the light source is focused in the sample by the objective lens, and as a result the photon density at the collection position is increased and fluorescence is generated due to the multi-photon excitation effect. A two-dimensional fluorescence image can be obtained by changing the collection position of the ultrashort pulse laser light by operating the scanner.

In this case, although the multi-photon excitation effect cannot be generated a second time even though ultrashort-pulse laser light that has been transmitted through the sample is returned by the retroreflective member and is incident on the sample a second time, among fluorescence generated when the ultrashort-pulse laser light is incident the first time, fluorescence emitted toward the opposite side from the objective lens is returned by the retroreflective member, is transmitted through the sample, and is collected by the objective lens, and therefore the amount of detected fluorescence can be increased and observation can be performed using a bright fluorescence image.

In the above-described aspect, the illumination light may be ultrashort-pulse laser light, and the illumination optical system may include a scanner that causes the ultrashort-pulse laser light to be scanned over the sample via the objective lens, and the illumination optical system may cause a higher harmonic to be generated at a scanning position of the ultrashort-pulse laser light in the sample.

With this configuration, when the sample is irradiated with ultrashort-pulse laser light, a ½ wavelength harmonic (SHG) and a ⅓ wavelength harmonic (THG) are induced by a non-linear optical effect in a specific component inside the sample, and therefore the sample can be observed without the use of fluorescent labeling via the detection of these harmonics. In this case, although there are many components that are generated in such a direction as to be transmitted through the sample among the generated harmonics, the generated components can be returned toward the light source side by the retroreflective member. Therefore, the harmonics can be collected by the objective lens, which collects the ultrashort-pulse laser light, and a compact observation device for a higher-harmonic image can be formed.

REFERENCE SIGNS LIST 1, 28 observation device
2 light source
3 illumination optical system (dark-field illumination optical system, excitation illumination optical system)
4 objective lens
5 detection optical system
6 retroreflective member
7 optical filter
11 scanner
14 confocal pinhole (pinhole)
20 reflective element
23 pinhole
24 confocal disk
29 polarizer
30 birefringent element
31 analyzer
32 ring slit (aperture)
33 phase film
36 light-reducing member
X sample

The invention claimed is:

1. An observation device comprising:
an illumination optical system that irradiates a transparent sample with illumination light from a light source;
an objective lens that collects observation light from the sample;
a detection optical system that detects the observation light collected by the objective lens; and
a retroreflective member that is arranged opposite the objective lens with the sample interposed therebetween and in which a plurality of very small reflective elements are arrayed;
wherein the sample is a cell that is accommodated together with a culturing liquid inside a culture vessel, and
wherein the objective lens and the illumination optical system are arranged below the sample in the direction of gravity.

2. The observation device according to claim 1, wherein the illumination optical system is a dark-field illumination optical system that irradiates the sample with the illumination light without the illumination light passing through the objective lens.

3. The observation device according to claim 1, wherein the illumination optical system is an excitation illumination optical system that causes fluorescence to be generated by irradiating the sample with the illumination light without the illumination light passing through the objective lens.

4. The observation device according to claim 1, wherein the illumination optical system irradiates the sample with the illumination light via the objective lens.

5. The observation device according to claim 4, wherein the illumination optical system includes an aperture that is arranged at a position that is optically conjugate with the pupil position of the objective lens, and
the detection optical system includes a phase film that is arranged at the pupil position of the objective lens or a position that is optically conjugate with the pupil position and has a shape that corresponds to the shape of the aperture.

6. The observation device according to claim 4, wherein the illumination optical system includes a polarizer,
the observation device further comprises a birefringent element that is close to the pupil position of the objective lens, and allows the illumination light that has been transmitted through the polarizer to be transmitted therethrough and allows the observation light from the sample that has been collected by the objective lens to be transmitted therethrough, and
the detection optical system includes an analyzer that allows the observation light from the sample that has been transmitted through the birefringent element to be transmitted therethrough.

7. The observation device according to claim 4, wherein the illumination optical system includes an aperture that is arranged at a position that is optically conjugate with the pupil position of the objective lens and irradiates the sample with the illumination light at a specific angle.

8. The observation device according to claim 7, wherein the detection optical system includes a light-reducing member close to a position that is optically conjugate with the pupil position of the objective lens.

9. The observation device according to claim 4, wherein the illumination optical system causes fluorescence to be generated by irradiating the sample with the illumination light.

10. The observation device according to claim 9, further comprising: a confocal disk that is arranged at a position that is optically conjugate with the focal position of the objective lens and includes a plurality of pinholes that allow the illumination light and the observation light to be transmitted therethrough.

11. The observation device according to claim 9, wherein the illumination light is laser light,
the illumination optical system includes a scanner that causes the laser light to be scanned over the sample via the objective lens, and
the detection optical system includes a pinhole that is arranged at a position that is optically conjugate with the focal position of the objective lens and that allows the fluorescence that has been generated at a scanning position of the laser light in the sample and has returned via the objective lens and the scanner to pass therethrough.

12. The observation device according to claim 9, further comprising: an optical filter that is arranged between the sample and the retroreflective member and blocks the fluorescence generated in the sample.

13. The observation device according to claim 9, wherein the illumination light is ultrashort-pulse laser light, and
the illumination optical system includes a scanner that causes the ultrashort-pulse laser light to be scanned over the sample via the objective lens.

14. The observation device according to claim 4, wherein the illumination light is ultrashort-pulse laser light, and
the illumination optical system includes a scanner that causes the ultrashort-pulse laser light to be scanned over the sample via the objective lens, and the illumination optical system causes a higher harmonic to be generated at a scanning position of the ultrashort-pulse laser light in the sample.

15. An observation device comprising:
an illumination optical system that irradiates a transparent sample with illumination light from a light source;

an objective lens that collects observation light from the sample;
a detection optical system that detects the observation light collected by the objective lens; and
a retroreflective member that is arranged opposite the objective lens with the sample interposed therebetween and in which a plurality of very small reflective elements are arrayed;
wherein the objective lens and the illumination optical system are arranged below the sample in the direction of gravity and the illumination optical system is a dark-field illumination optical system that irradiates the sample with the illumination light without the illumination light passing through the objective lens.

16. An observation device comprising:
an illumination optical system that irradiates a transparent sample with illumination light from a light source;
an objective lens that collects observation light from the sample;
a detection optical system that detects the observation light collected by the objective lens; and
a retroreflective member that is arranged opposite the objective lens with the sample interposed therebetween and in which a plurality of very small reflective elements are arrayed;
wherein the objective lens and the illumination optical system are arranged below the sample in the direction of gravity,
the illumination optical system irradiates the sample with the illumination light via the objective lens,
the illumination optical system includes an aperture that is arranged at a position that is optically conjugate with the pupil position of the objective lens, and
the detection optical system includes a phase film that is arranged at the pupil position of the objective lens or a position that is optically conjugate with the pupil position and has a shape that corresponds to the shape of the aperture.

17. An observation device comprising:
an illumination optical system that irradiates a transparent sample with illumination light from a light source;
an objective lens that collects observation light from the sample;
a detection optical system that detects the observation light collected by the objective lens; and
a retroreflective member that is arranged opposite the objective lens with the sample interposed therebetween and in which a plurality of very small reflective elements are arrayed;
wherein the objective lens and the illumination optical system are arranged below the sample in the direction of gravity,
the illumination optical system includes a polarizer,
the illumination optical system irradiates the sample with the illumination light via the objective lens,
the observation device further comprises a birefringent element that is close to the pupil position of the objective lens, and allows the illumination light that has been transmitted through the polarizer to be transmitted therethrough and allows the observation light from the sample that has been collected by the objective lens to be transmitted therethrough, and
the detection optical system includes an analyzer that allows the observation light from the sample that has been transmitted through the birefringent element to be transmitted therethrough.

18. An observation device comprising:
an illumination optical system that irradiates a transparent sample with illumination light from a light source;
an objective lens that collects observation light from the sample;
a detection optical system that detects the observation light collected by the objective lens; and
a retroreflective member that is arranged opposite the objective lens with the sample interposed therebetween and in which a plurality of very small reflective elements are arrayed;
wherein the objective lens and the illumination optical system are arranged below the sample in the direction of gravity,
the illumination optical system includes an aperture that is arranged at a position that is optically conjugate with the pupil position of the objective lens and irradiates the sample with the illumination light via the objective lens at a specific angle, and
the detection optical system includes a light-reducing member close to a position that is optically conjugate with the pupil position of the objective lens.

19. An observation device comprising:
an illumination optical system that irradiates a transparent sample with illumination light from a light source;
an objective lens that collects observation light from the sample;
a detection optical system that detects the observation light collected by the objective lens; and
a retroreflective member that is arranged opposite the objective lens with the sample interposed therebetween and in which a plurality of very small reflective elements are arrayed; and
a confocal disk that is arranged at a position that is optically conjugate with the focal position of the objective lens and includes a plurality of pinholes that allow the illumination light and the observation light to be transmitted therethrough,
wherein the objective lens and the illumination optical system are arranged below the sample in the direction of gravity, and
the illumination optical system causes fluorescence to be generated by irradiating the sample with the illumination light via the objective lens.

20. An observation device comprising:
an illumination optical system that irradiates a transparent sample with illumination light from a light source;
an objective lens that collects observation light from the sample;
a detection optical system that detects the observation light collected by the objective lens; and
a retroreflective member that is arranged opposite the objective lens with the sample interposed therebetween and in which a plurality of very small reflective elements are arrayed;
wherein the objective lens and the illumination optical system are arranged below the sample in the direction of gravity,
the illumination optical system causes fluorescence to be generated by irradiating the sample with the illumination light via the objective lens,
the illumination light is laser light,
the illumination optical system includes a scanner that causes the laser light to be scanned over the sample via the objective lens, and
the detection optical system includes a pinhole that is arranged at a position that is optically conjugate with the focal position of the objective lens and that allows the fluorescence that has been generated at a scanning position of the laser light in the sample and has returned via the objective lens and the scanner to pass therethrough.

21. An observation device comprising:

an illumination optical system that irradiates a transparent sample with illumination light from a light source;

an objective lens that collects observation light from the sample;

a detection optical system that detects the observation light collected by the objective lens; and a retroreflective member that is arranged opposite the objective lens with the sample interposed therebetween and in which a plurality of very small reflective elements are arrayed;

wherein the objective lens and the illumination optical system are arranged below the sample in the direction of gravity, the illumination optical system irradiates the sample with the illumination light via the objective lens, and the illumination light is ultrashort-pulse laser light, and the illumination optical system includes a scanner that causes the ultrashort-pulse laser light to be scanned over the sample via the objective lens, and the illumination optical system causes a higher harmonic to be generated at a scanning position of the ultrashort-pulse laser light in the sample.

\* \* \* \* \*